United States Patent [19]

Hogendijk

[11] Patent Number: 5,382,253
[45] Date of Patent: Jan. 17, 1995

[54] CLIP APPLIER TOOL

[75] Inventor: Michael Hogendijk, Sunnyvale, Calif.

[73] Assignee: Unisurge, Inc., Cupertino, Calif.

[21] Appl. No.: 27,012

[22] Filed: Mar. 5, 1993

[51] Int. Cl.⁶ .............................................. A61B 17/00
[52] U.S. Cl. ................... 606/142; 606/139; 227/901
[58] Field of Search ............... 606/139, 142, 143, 151, 606/205–208, 210, 211; 604/35; 227/901; 29/243.56

[56] References Cited

U.S. PATENT DOCUMENTS

| | | | |
|---|---|---|---|
| 4,038,987 | 8/1977 | Komiya | 606/142 |
| 4,096,864 | 6/1978 | Kletschka et al. | 606/211 |
| 4,562,839 | 1/1986 | Blake III et al. | |
| 4,662,374 | 5/1987 | Blake, III | 606/143 |
| 4,887,612 | 12/1989 | Esser et al. | 606/208 |
| 4,919,152 | 4/1990 | Ger | 606/142 |
| 5,049,153 | 9/1991 | Nakao et al. | 606/151 |
| 5,147,373 | 9/1992 | Ferzli | 606/148 |
| 5,176,702 | 1/1993 | Bales et al. | 606/206 |
| 5,199,566 | 4/1993 | Ortiz et al. | 606/142 |
| 5,209,747 | 5/1993 | Knoepfler | 606/205 |
| 5,263,967 | 11/1993 | Lyons III et al. | 606/205 |

FOREIGN PATENT DOCUMENTS 0116220 8/1984 European Pat. Off. ............ 606/143
419087 11/1934 United Kingdom ................ 606/139

OTHER PUBLICATIONS

Page CA 1 of Storz Brochure entitled "Suture and Ligature" extracted from Catalog Endoscopic Surgery 2nd Edition Jan. 1993.

Primary Examiner—Stephen C. Pellegrino
Assistant Examiner—Jeffrey A. Schmidt
Attorney, Agent, or Firm—Flehr, Hohbach, Test, Albritton & Herbert

[57] ABSTRACT

A clip applier tool comprising an elongate tubular member having a bore extending therethrough and having proximal and distal extremities. A push rod is slidably mounted in the bore and has proximal and distal extremities. An actuator is mounted in said bore in said tubular member. The actuator means is connected to the distal extremity of the push-pull rod. First and second clip applier jaw members are mounted in the bore in said tubular member and have proximal and distal extremities. A pivotal connection connects the proximal extremities of the jaw members to the distal extremity of the actuator.

11 Claims, 4 Drawing Sheets

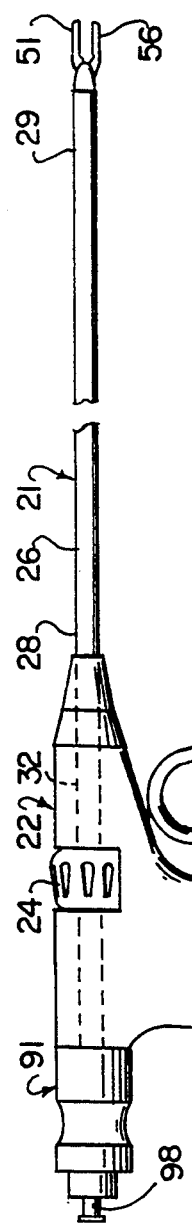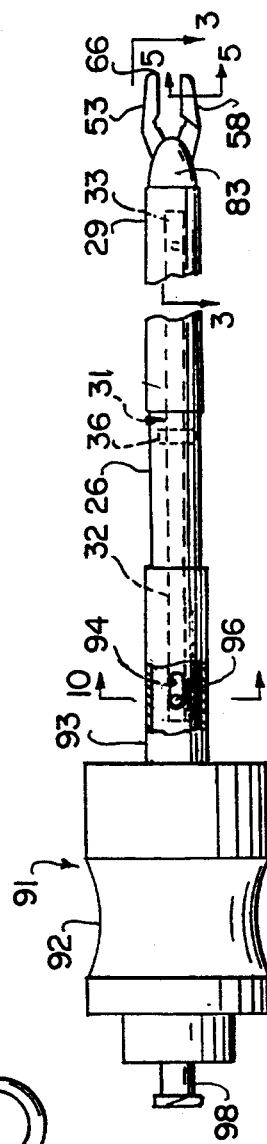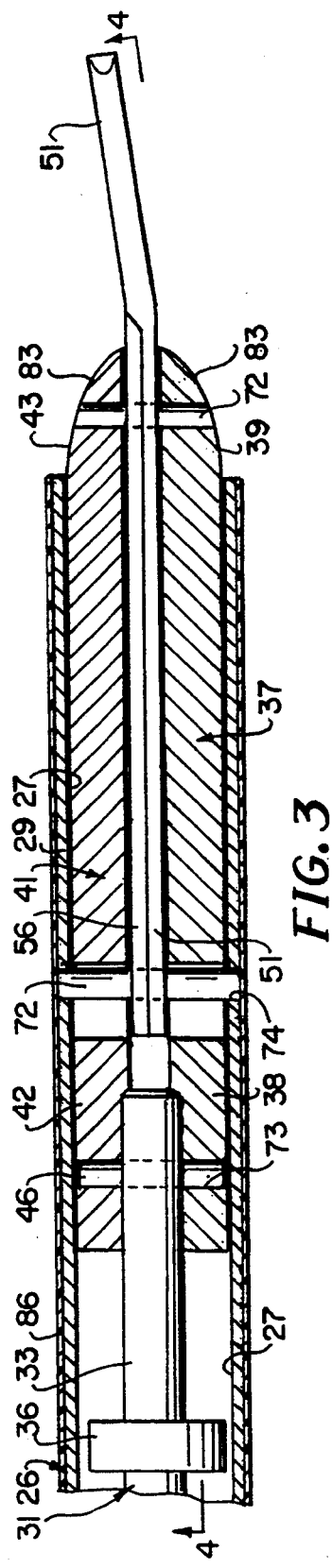

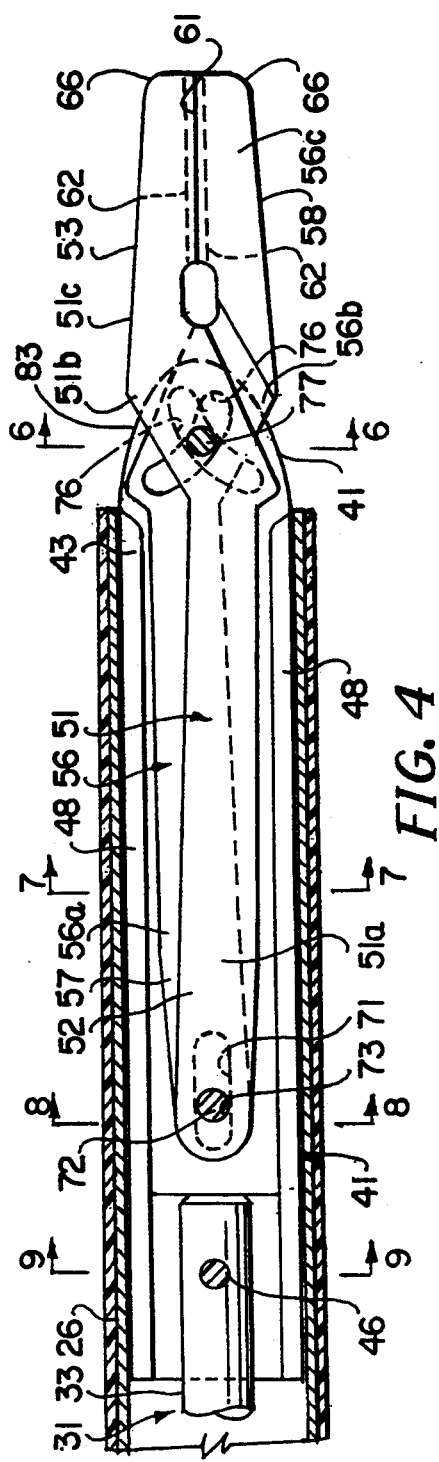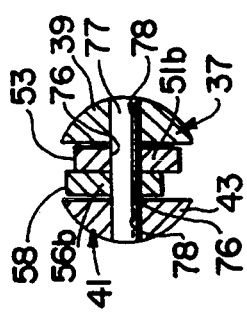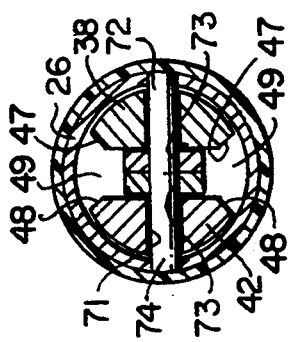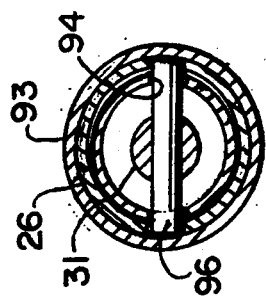

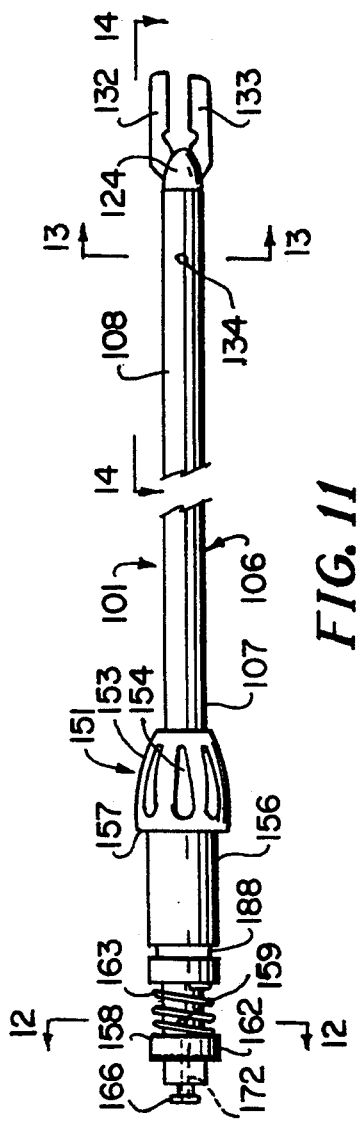
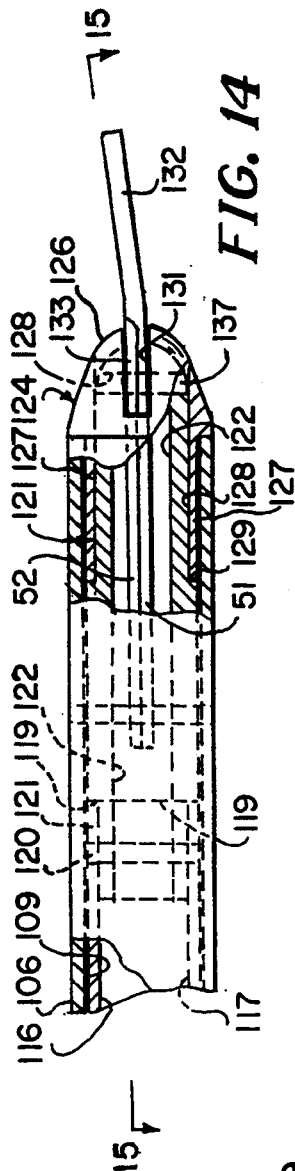
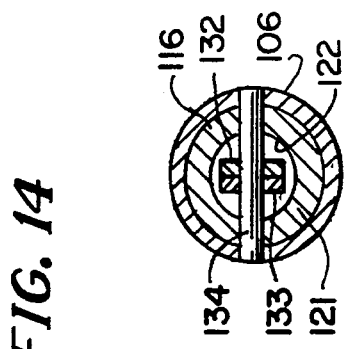
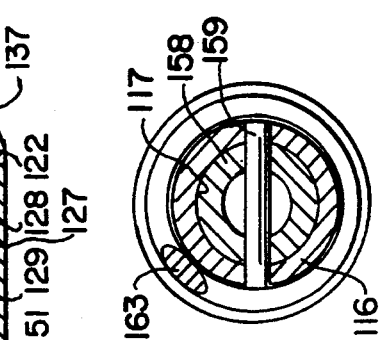
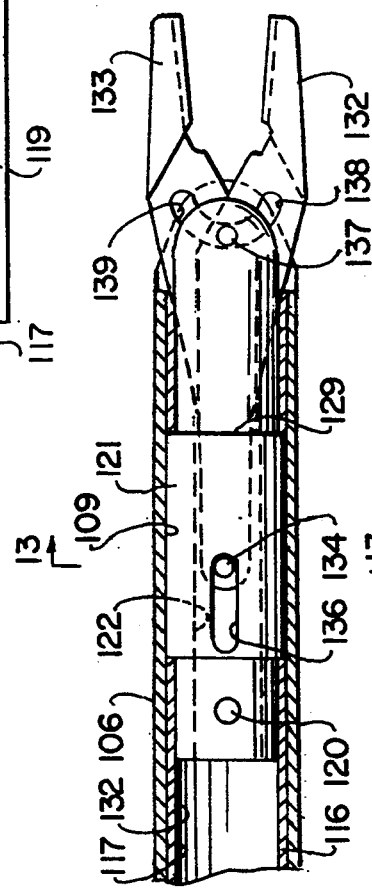

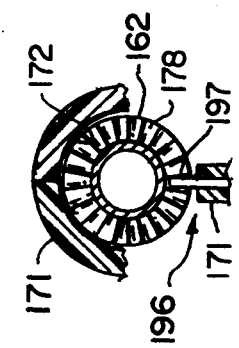
FIG. 19
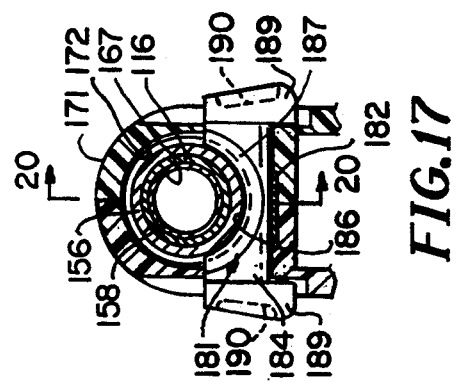
FIG. 17
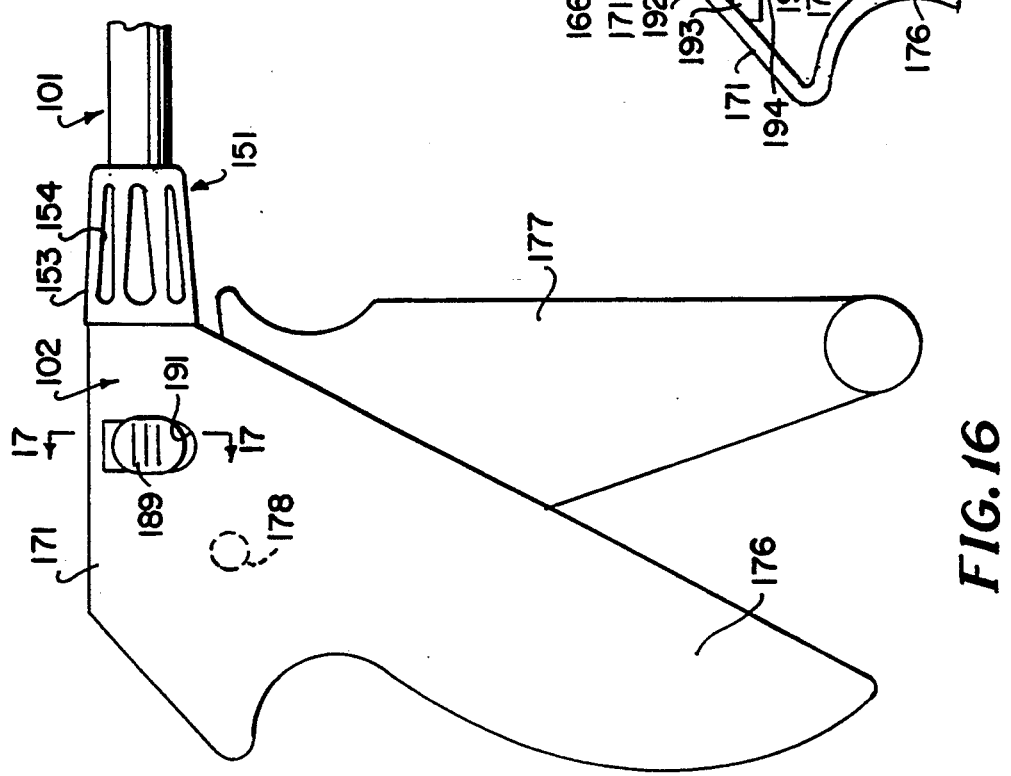
FIG. 20
FIG. 18
FIG. 16

CLIP APPLIER TOOL

This invention relates to a clip applier tool and more particularly to a clip applier tool for use in laparoscopic surgical procedures.

Clip appliers heretofore made for use in open surgical procedures have been of a scissors type. Single shot clip appliers have also been provided for use in laparoscopic procedures typically of a 10 millimeter size which can be utilized for applying a single clip at a time. Multi-shot clip appliers have been provided also typically of a 10 millimeter size for delivering multiple clips for use in laparoscopic surgical procedures. All of such clip appliers have a complicated construction and are relatively expensive. There is therefore need for a single clip applier which is much less expensive and which can be readily manufactured.

In general, it is an object of the present invention to provide a clip applier tool which can be utilized for applying a single clip at a time.

Another object of the invention is to provide a clip applier tool of the above character which can be reutilized.

Another object of the invention is to provide a clip applier tool of the above character which can be readily cleaned.

Another object of the invention is to provide a clip applier tool of the above character which can be readily manufactured.

Additional features and objects of the invention will appear from the following description in which the preferred embodiments are set forth in detail in conjunction with the accompanying drawings.

FIG. 1 is a side-elevational view of a clip applier tool incorporating the present invention mounted in a gun-type handle.

FIG. 2 is a side-elevational view partially in cross section of the clip applier tool shown in FIG. 1.

FIG. 3 is an enlarged cross-sectional view taken along the line 3—3 of FIG. 2.

FIG. 4 is an enlarged cross-sectional view taken along the line 4—4 of FIG. 3.

FIG. 5 is a cross-sectional view taken along the line 5—5 of FIG. 2.

FIG. 6 is a cross-sectional view taken along the line 6—6 of FIG. 4.

FIG. 7 is a cross-sectional view taken along the line 7—7 of FIG. 4.

FIG. 8 is a cross-sectional view taken along the line 8—8 of FIG. 4.

FIG. 9 is a cross-sectional view taken along the line 9—9 of FIG. 4.

FIG. 10 is a cross-sectional view taken along the line 10—10 of FIG. 2.

FIG. 11 is an alternative embodiment of a clip applier tool incorporating the present invention.

FIG. 12 is a cross-sectional view looking along the line 12—12 of FIG. 11.

FIG. 13 is a cross-sectional view taken along the line 13—13 of FIG. 11.

FIG. 14 is a view, partially in cross section, looking along the line 14—14 of FIG. 11.

FIG. 15 is a cross-sectional view looking along the line 15—15 of FIG. 14.

FIG. 16 is a side-elevational view of the clip applier tool shown in FIG. 11 mounted in a gun-type handle incorporating the present invention.

FIG. 17 is a cross-sectional view looking along the line 17—17 of FIG. 16 and also along line 17—17 of FIG. 18.

FIG. 18 is a partial side-elevational view similar to FIG. 16 but showing certain portions of the gun broken away.

FIG. 19 is a cross-sectional view taken along the line 19—19 of FIG. 18.

FIG. 20 is a cross-sectional view taken along the line 20—20 of FIG. 17.

In general, the clip applier tool incorporating the present invention is comprised of a elongate tube having a bore extending therethrough. A push rod is slidably mounted in the bore and has proximal and distal extremities. First and second actuator members are slidably mounted in the bore in the tube and have proximal and distal extremities. Pin means is provided for pivotally connecting the proximal extremities of the first and second actuator members to the distal extremity of the push rod. First and second clip applier jaw members are slidably mounted in the bore in said tube and have proximal and distal extremities. The distal extremities of the clip applier jaw members have opposing jaw portions formed therein. Pin and slot means is provided for interconnecting the proximal extremities of clip applier jaw members to the first and second actuator members the distal of the proximal extremities of the first and second actuator members. Each of the clip applier jaw members has an arcuate slot formed therein. A pivot pin means is provided which extends through the slots in the clip applier jaw members to interconnect the same. Means is provided which is secured to the distal extremity of the tube to retain the pivot pin means extending through said slots. Means is secured to the proximal extremity of the tube for causing rectilinear movement of the push rod in said tube to cause movement of the clip applier jaw members to cause said jaw portions to move between open and closed positions with respect to each other.

More particularly as shown in FIGS. 1–10 of the drawings, the clip applier tool 21 incorporating the present invention is shown mounted in a gun-type handle 22 of the type described in co-pending application, Ser. No. 07/806,666, filed Dec. 13, 1991. The clip applier 21 is constructed in the same manner as other tools described in said co-pending application, Ser. No. 07/806,666, filed Dec. 13, 1991 and is adapted to be actuated by the trigger 23 provided as a part of the handle 22 as hereinafter described.

The clip applier 21 is comprised of an elongate rigid tube 26 formed of a suitable material such as stainless steel which can have a suitable outside diameter, as for example 10 millimeters but preferably a smaller diameter, as for example 8 millimeters. The tube 26 is provided with a bore 27 extending longitudinally therethrough. The tube 26 is provided with proximal and distal extremities 28 and 29. A push-pull rod 31 is slidably mounted in the bore 27 and is provided with proximal and distal extremities 32 and 33. A plurality of collars 36 are provided on the rod 31 and are spaced longitudinally of the rod and serve to guide the rod 31 in the bore 27.

A first actuator member 37 having proximal and distal extremities 38 and 39 and a second actuator member 41 having proximal and distal extremities 42 and 43 are slidably mounted in the bore 27 of the tube 26. The first and second actuator members can be formed of a suitable material such as ULTEM 1000. Means is provided for pivotally connecting the proximal extremities 38 and 42 of the first and second actuator members 37 and 41 to the distal extremity 33 of the push-pull rod 31 and consists of pin 46 which extends through the first and second actuator members 37 and 41 and the push-pull rod 31. As shown in FIGS. 6, 7, 8 and 9, the first and second actuator members 37 and 41 are substantially semi-circular in cross-section to provide additional rigidity to the first and second actuator members 37 and 41. Beveled surfaces 47 and 48 are provided on the actuator members 37 and 41 extending the length thereof which form liquid flow passages 49 used for a purpose hereinafter described.

A first jaw member 51 having proximal and distal extremities 52 and 53 and a second jaw member 56 having proximal and distal extremities 57 and 58 are slidably mounted in the bore 27 of the tube 26. The distal extremities 53 and 58 of the first and second jaw members 51 and 56 are provided with opposed serrated jaw surfaces 61 which are adapted to move between open and closed positions with respect to each other as hereinafter described. The jaw surfaces 61 are inclined at a suitable angle with respect to the horizontal, as for example approximately 3° extending in a distal direction.

Longitudinally extending clip receiving substantially V-shaped recesses 62 are provided in the distal extremities 53 and 58 and extend through the jaw surfaces 61 (see FIG. 5). The V-shaped recesses 62 can have a suitable included angle, as for example approximately 60°±2°. The first and second jaw members 51 and 56 are formed of a suitable material such as stainless steel. The first and second jaw members 51 and 56 are provided with portions 51a, 51b, 51c and 56a, 56b and 56c, respectively. The portions 51a and 56a are elongate and are relatively straight and extend from the proximal extremities 52 and 57 to an intermediate portions 51b and 56c which extend at a suitable angle, as for example approximately 25°–40° and preferably approximately 30° as shown with respect to the elongate portions 51a and 56b. The portions 51c and 56c extend in a direction which is substantially parallel to the direction of the portions 51a and 56a. The portions 51c and 56c are provided with rounded forward extremities 66.

Pin and slot means is provided for forming an interconnection between the proximal extremities 52 and 57 of the first and second jaw members 51 and 56 and as shown takes the form of elongate slots 71 in the proximal extremities 38 and 42 of the first and second actuator members 37 and 41. The slots 71 extend in a direction which is substantially parallel to the longitudinal axis of the first and second actuator members 37 and 41. The slots 71 cooperate with a pin 72 which extends through the slots 71 and are perpendicular to the planes of the first and second actuator members 37 and 41 and extend through holes 73 provided in the proximal extremities 52 and 57 of the first and second jaw members 51 and 56. The pin 72 also extends through holes 74 provided in the sidewall forming the tube 26 to retain it in a fixed position longitudinally of the tube 26.

Additional pin and slot means is provided for interconnecting the intermediate portions 51b and 56b of the first and second jaw members 51 and 56 with the distal extremities 39 and 43 (see FIG. 6) of the first and second actuator members 37 and 41 and consists of arcuate slots 76 provided in the intermediate portions 51b and 56b. A cylindrical pin 77 extends through the slots 76 and through holes 78 provided in the distal extremities 39 and 43 of the first and second actuator members 37 and 41. The distal extremities 51c and 56c of the jaw members 51 and 56 are bent in one direction at a suitable angle in a range from 5° to 15° and preferably about 8° from the horizontal axis as shown in FIG. 3.

The distal extremities of the actuator members 37 and 41 are provided with generally rounded surfaces 83 as shown in the drawing which extend distally of the tubular member 26.

A sheath 86 is provided formed of a suitable material such as a heat shrinkable plastic which covers the outer surface of the tube 26 and extends the length thereof.

The proximal extremity 20 of the tube 26 of the clip applier tool 21 is connected to a cap assembly 91 of the type described in co-pending application, Ser. No. 07/806,666, filed Dec. 13, 1991 so that the clip applier tool 21 is adapted to cooperate with the handle 22. Thus, as is disclosed in said co-pending application, the cap assembly 91 is provided with an exterior cap 92 from which there extends a tubular member 93 that receives the tube 26. Pin and slot means is provided for forming a connection between the push-pull rod 31 and the tube 26 and consists of slots 94 provided in the tube 26 and through which a pin 96 extends and mounted in the push-pull rod 31 as shown particularly in FIGS. 2 and 10. A Luer-type fitting 98 is mounted on the cap 92.

Operation and use of the clip applier 21 with the hand gun as shown in FIG. 1 may now be briefly described as follows. By way of example let it be assumed that the surgeon in a surgical laparoscopic procedure wishes to clip off the common bile duct. The clip applier tool 21 is slipped into the handle 22 so that the tube 26 extends through the handle 22 and the cap 82 snaps onto the handle 22. Thereafter the surgeon grasps the handle 22 by either of the right or left hand. The jaws 51 and 56 are moved to an open position by the fingers of the surgeon's hand holding the handle 22 which are moved to move the trigger 23 forwardly. The surgeon then positions the handle 22 to move the distal extremity of the clip applier tool 21 so that the jaw surfaces 61 advanced into a conventional cassette which normally contains a plurality of the clips. The jaw surfaces 61 of the clip applier tool 21 are advanced over a clip in the cassette until the tool bottoms out on the selected clip after which the clip applier tool 21 can be removed bringing with it the selected clip seated within the V-shaped recesses 62 of the jaw surfaces 61. The V-shaped recesses 62 provided in the jaws 51 and 56 ensure that the clip is retained in a plane extending through the jaw surfaces as forces are being applied to close the clip.

The handle 22 can then be moved to cause the distal extremity of the clip applier tool 21 to be advanced through a trocar already positioned in the body of the patient. The advance of the clip applier tool 21 can be observed through visual means normally provided in laparoscopic procedures. During positioning of the clip applier tool 21, the clip applier tool 21 can be rotated by operation of the knob 24 provided on the handle 22. The surgeon advances the first and second jaw members 51 and 56 over the bile duct and then squeezes or pulls the trigger 23 rearwardly to cause deformation of the clip and to bring the jaws 51 and 56 together to clamp onto the bile duct. As soon as this has been accomplished, the trigger 23 can be released and the jaws 51 and 56 are moved to an open position by movement of the trigger 23. The clipper applier can then be removed. If additional clips are needed to complete the surgical procedure, the same procedure as hereinbefore described can be utilized to apply one clip at a time until the necessary amount of clips have been put in place.

It has been found that the clip applier of the present invention is constructed in a manner so that it is strong enough to readily deform the clips to move the same into a clamping position. In doing so, the jaw surfaces 61 move in directions which are nearly parallel to each other when closing which facilitates the application of the clips. It has been found that with the clip applier tool 21 of the present invention it is possible to apply a minimum of 15 lb. per square inch at the tip of the jaw surfaces 61 and as much as 21 lbs. per square inch.

The mechanism utilized in the clip applier tool 21 for closing the clips is inherently stronger than a toggle mechanism. The semi-circular cross section of the first and the second actuator members 37 and 41 and of the jaw portions of the first and second jaw members 51 and 56 are relatively massive to provide the strength needed for closing of the clips. The first and second actuator members 37 and 41 are supported on all sides. The connecting pins 46, 72 and 77 utilized are of sufficient diameter so there is no shifting or flexing of the pins during closing of a clip.

Another embodiment of a clip applier tool 101 incorporating the present invention is shown in FIG. 11 and is utilizable with a stand alone gun-type handle 102 as shown in FIG. 17.

The clip applier tool 101 has a construction similar to the clip applier tool 21 hereinbefore described. Thus, there is provided a relatively rigid elongate tubular member 106 corresponding to the tube 26. It has proximal and distal extremities 107 and 108 and a bore 109 which extends therethrough. A push-pull tube 116 is slidably mounted in the bore 109 and is provided with a bore 117 extending therethrough. The distal extremity of the push-pull tube 116 is mounted in an annular recess 119 of an actuator member 121 and is secured thereto by a pin 120. The actuator member 121 is slidably mounted in the bore 109 of the elongate tubular member 106 and is provided with a bore 122 extending therethrough which is in communication with the bore 117 of the push-pull tube 116. A nose piece 124 having a rounded portion 126 and a cylindrical portion 127 is provided with a bore 128 extending therethrough. The nose piece 124 is formed of a suitable material such as ULTEM 1000. The cylindrical portion 127 is fitted within the bore 109 of the elongate tubular member 106 and in an annular recess 129 formed in the actuator member 121 and is retained therein by crimping the tubular member 106 onto the cylindrical portion 127. The rounded portion 126 of the nose piece 124 is provided with a diametrically extending slot 131 which opens into the bore 122 and in which first and second jaw members 132 and 133 of the type similar to that hereinbefore described are mounted and are pivotally connected by pin 134 extending through slots 136 provided in the actuator member 121. A pin 137 is mounted in the nose piece 124 and extends through arcuate slots 138 and 139 provided in the first and second jaw members 132 and 133.

A base member 151 is secured to the proximal extremity 107 of the elongate tubular member or tube 106. The base member 151 is generally cylindrical (see FIG. 11) and is provided with an internal bore 152 through which the push-pull tube 116 extends. The base member 151 is provided with a rounded cylindrical surface 153 having circumferentially spaced apart indentations 154. The base member 151 has a cylindrical extension 156 of reduced diameter extending approximately from the surface 153 so that there is provided a shoulder 157 between the junction of the extension 156 and the rounded surface 153. A cylindrical plunger 158 is mounted in the bore 117 of the proximal end of the push-pull tube 116 and is secured by a pin 159. Yieldable spring means in the form of a coil spring 163 is mounted on the proximal end of the push-pull rod 116 and has one end engaging the cylindrical extension 156 and has the other end engaging a cylindrical member 158. A Luer-type fitting 166 which is utilized for a purpose hereinafter described is formed as a part of the plunger 158 and is in communication with a bore 167 in the plunger 158. The bore 167 opens into the bore 152 of the base member 151 and into the bore 117 of the push-pull rod 116.

The clip applier tool 101 is adapted to be mounted in a gun-type handle 102 as shown in FIGS. 17-20. As shown therein, the handle 102 is comprised of a housing 171 which is provided with a bore 172 adapted to receive the clip applier tool 101. The housing 171 is formed integral with a depending handle portion 176 which is adapted to be engaged by the palm of a human hand and is shaped appropriately. A trigger 177 depends from the housing 171 and is pivotally mounted on a pivot pin 178 extending through the handle piece 176 permitting the trigger 177 to be moved towards the handle piece 176 by the fingers of the hand holding the handle assembly 102. The trigger 177 is provided with an abutment 179 which is adapted to engage the collar 162 of the clip applier tool 101 for movement against the force of spring 163.

Means is provided for releasably receiving the clip applier tool 101 within the handle assembly 102 and consists of latch-type release means 181 mounted in the housing 171 which consists of a spring member 182 in the form of a leaf spring which is substantially planar as shown and which is retained in opposed slots 183 provided in the housing 171. The spring member 182 yieldably engages a latching member 184 generally in the form of a planar plate which extends transversely of the bore 172 and which is provided with a semi-circular recess 186. The latching member 184 is provided with a chamfered leading edge 187 (see FIG. 21). The recess 186 and latching member 184 are sized so that they can enter an annular recess 188 provided in the extension 156 to latch the clip applier tool 101 within the handle assembly 102. Finger knobs 189 are mounted on opposite ends of the latching member 184 and are provided with finger-type recesses 190 therein which are adapted to receive a finger of the hand. As shown particularly in FIGS. 16 and 17, the knobs 189 are generally oval in shape and are adapted to move vertically with respect to the housing 151 within slightly larger oval recesses 191 provided on opposite sides of the housing 171 so that in the uppermost positions of the knobs 189 in the recesses 191, the latching member 184 is in engagement with the annular recess 188. Upon downward movement of both of the knobs 189 by the fingers of the hand, the latching member 184 can be easily moved sufficiently far against the force of the spring 182 so that the extension 156 with its annular recess 188 therein clears the latching member 184 so that the clip applier tool 101 can be removed and inserted. When the clip applier tool 101 is inserted into the housing 171, a plug 192 of a suitable material such as ULTEM enters the bore 167 of the Luer-type fitting 166 and seals off the bore. The plug 192 is carried by the housing 171 and is retained in bosses 193 and 194 formed as a part of the housing 171.

The latch-type release means 181 hereinbefore described permits rotational movement of the clip applier tool 101 whenever that is desired by the physician. This can be accomplished by the physician using one hand to hold the handle piece 176 and trigger 177 while using the other hand to rotate the clip applier tool 101. The clip applier tool 101 can be rotated in either a counterclockwise or clockwise direction with its movement being yieldably restrained by a detent-type mechanism 196 which consists of a pin 197 mounted in the trigger 177 which yieldably engages radially extending recesses 178 provided on the collar 162. Thus, it can be seen that the surgeon can readily rotate the clip applier tool 101 to the desired angular position by engaging the indentations 154 on the base member 151. The detent means will then retain the tool 101 in the desired angular position because of this relationship.

Operation of the clip applier tool 101 with the handle assembly 102 is very similar that hereinbefore described with respect to the clip applier tool 21 and the handle 22. With the construction shown, the spring 163 yieldably urges the push-pull rod 116 proximally to maintain the jaw members 132 and 133 in a normally open position with a clip therein. When the clip applier tool 101 is introduced during a typical laparoscopic procedure, the insufflation gas is prevented from escaping from the patient because the bore 167 is sealed by the plug 192. When it is desired to apply the clip, the jaw members 132 and 133 can be moved to a closed position by the surgeon's hand grasping the handle piece 176 and pulling the trigger 177 proximally against the force of the spring 163. The clip applier tool 101 can be rotated to the desired position by the other hand of the surgeon against the force of the detent-type retention means 196 and retained in the desired rotational position during application of the clip.

When the procedure has been completed, the clip applier tool 101 can be readily removed by taking the fingers of one hand and pushing downwardly on the knobs 189 to move the latching member 184 downwardly against the force of the spring 182 so that it clears the annular recess 188 provided in the extension 156. As soon as this has been accomplished, the clip applier tool 101 can be removed from the handle assembly 102. Thereafter, the clip applier tool can be readily cleaned by attaching a Luer-type fitting to the Luer-type fitting 166 and introducing a saline solution through the bore 167 in the plunger 158 and into the bore 117 of the push-pull rod 116 and into the bore 122 of the actuator member 121 and the slot 131 of the nose piece 124 and to pass between and over the first and second jaw members 132 and 133 to clean the same.

It is apparent from the foregoing that there has been provided a new and improved clip applier tool and a gun-type handle for use therewith which facilitates the application of clips in endoscopic procedures and particularly in laparoscopic procedures. The surgeon can readily apply forces which are more than adequate to cause clamping of the clips. The clips can be easily removed from packages of clips and can be readily inserted through trocars for application of the clips. The clip applier tool can be rotated to the desired position. The necessary forces for clamping or closing of the clips can be readily applied. The tool is constructed in such a manner so that it can readily accommodate the relatively large closing forces which are required but which has limits which permit closing of the clips but prevent overtravel in the tool. With the mechanism provided, it is readily possible to obtain ratios as large as 8-to-1 and to transfer such forces down the barrel or tube to the clip itself. There are a few moving parts which facilitate sterilization and cleaning of the tool after use.

What is claimed is:

1. A clip applier tool for applying a clip inside of a body in a laparoscopic surgical procedure comprising an elongate tubular member having a bore extending therethrough and having proximal and distal extremities, a push-pull rod slidably mounted in said bore and having proximal and distal extremities, actuator means mounted in said bore and having circumferential surfaces engaging the inside of the distal extremity of said tubular member for slidable movement therein, means connecting the actuator means to the distal extremity of the push-pull rod, first and second clip applier jaw members having elongate proximal extremities extending through said actuator means and having distal extremities adapted for gripping the clip and pivotal means connecting the proximal extremities of the Jaw members to said tubular member to permit the distal extremities of the jaw members to move between open and closed positions, each of the Jaw members being provided with a slot formed therein between the proximal and distal extremities thereof and pin means extending through the slots and coupled to the actuator means so that as the push-pull rod is actuated the pin means travels through the slots to cause the jaw members to move between open and closed positions with respect to each other, the actuator means engaging the jaw members distal of the slots to inhibit shifting of the distal extremities of the jaw members during application of the clip.

2. A tool as in claim 1 further including handle means coupled to the elongate tubular member and the push-pull rod for causing rectilinear movement of the push-pull rod with respect to the elongate tubular member.

3. A tool as in claim 2 further including means carried by the elongate tubular member and the handle means for permitting rotational movement of the jaw members.

4. A tool as in claim 1 wherein said actuator means is in the form of a single member.

5. A tool as in claim 1 wherein said actuator means is in the form of first and second substantially parallel actuator members.

6. A tool as in claim 1 wherein the proximal extremity of the push-pull rod is provided with an annular recess, yieldable spring means disposed between the push-pull rod and the elongate tubular member for yieldably urging the push-pull member in a direction proximal of the distal extremity of the elongate tubular member and cooperative means carried by the elongate tubular member and the push-pull rod for limiting proximal movement of the push-pull rod with respect to the elongate tubular member.

7. A clip applier tool for applying a clip inside of a body in a laparoscopic surgical procedure comprising an elongate tubular member having a bore extending therethrough and having proximal and distal extremities, a push-pull rod slidably mounted in said bore and having proximal and distal extremities, actuator means slidably mounted in said bore in said tubular member, means connecting the actuator means to the distal extremity of the push-pull rod, first and second clip applier jaw members having proximal extremities mounted in the bore in said tubular member and having distal extremities adapted for gripping the clip and pivotal means connecting the proximal extremities of the jaw members to said tubular member to permit the distal extremities of the jaw members to move between open and closed positions, each of the jaw members being provided with a slot formed therein which is generally arcuate and curves toward the distal extremity of the respective jaw member and pin means extending through the slots and coupled to the actuator means whereby as the push-pull rod is actuated the jaw members are moved between open and closed positions with respect to each other, the jaw members moving between their open and closed positions at a rate and exerting closure forces on the clip during movement between their open and closed positions whereby the rate of closure decreases and the closure forces increase as the jaw members approach their closed position.

8. A clip applier tool for applying a clip inside of a body in a laparoscopic surgical procedure comprising an elongate tubular member having a bore extending therethrough and having proximal and distal extremities, the elongate tubular member having a diameter not greater than 10 millimeters, a push-pull rod slidably mounted in said bore and having proximal and distal extremities, actuator means slidably mounted in said bore in said tubular member for movement between first and second positions, means connecting the actuator means to the distal extremity of the push-pull rod, first and second clip applier jaw members having proximal extremities mounted in the bore in said tubular member within the actuator means and having distal extremities adapted for gripping clip, pivotal means connecting the proximal extremities of the jaw members, pin and slot means carried b the actuator means and the jaw members for opening and closing the distal extremities of the jaw members upon movement of the actuator means between its first and second positions and the actuator means engaging the jaw members distal of the slots during movement of the jaw members between their first and second positions to form means for inhibiting shifting of the distal extremities of the jaw member during application of the clip.

9. A tool as in claim 8 wherein the actuator means includes first and second actuator members which are generally semi-circular in cross-section.

10. A clip applier tool comprising an elongate tubular member having a bore extending therethrough and having proximal and distal extremities, a push-pull rod slidably mounted in said bore and having proximal and distal extremities, actuator means slidably mounted in said bore in said tubular member for movement between first and second positions, means connecting the actuator means to the distal extremity of the push-pull rod, first and second clip applier jaw members mounted in the bore in said tubular member and having proximal and distal extremities, pivotal means connecting the proximal extremities of the jaw members, pin and slot means carried by the actuator means and the jaw members for opening and closing the distal extremities of the jaw members upon movement of the actuator means between its first and second positions, the push-pull rod being provided with a bore extending therethrough and the actuator means including a bore in communication with the bore in the push-pull rod in communication with the first and second jaw members so that when a saline solution is introduced through the bore of the push-pull rod, the saline solution is introduced to the first and second jaw members to cleanse the same.

11. A clip applier tool comprising an elongate tubular member having a bore extending therethrough and having proximal and distal extremities, a push-pull rod slidably mounted in said bore and having proximal and distal extremities and a bore extending between its proximal and distal extremities, first and second clip applier jaw members mounted in the bore in said tubular member and having proximal and distal extremities, pivotal means connecting the proximal extremities of the jaw members to permit the distal extremities of the jaw members to move between open and closed positions, actuator means coupling the jaw members to the distal extremity of the push-pull rod and means mounted on the proximal extremity of the push-pull rod in communication with the bore of the push-pull rod for introducing a solution through the bore of the push-pull rod.

* * * * *